(12) United States Patent
Lambridis et al.

(10) Patent No.: US 11,964,033 B2
(45) Date of Patent: *Apr. 23, 2024

(54) DRY COMPOSITION FOR AND METHODS FOR FABRICATION OF DRY COMPOSITIONS

(71) Applicant: Mana Products, Inc., Long Island City, NY (US)

(72) Inventors: George Lambridis, Wayne, NJ (US); Julio Pina, Woodside, NY (US)

(73) Assignee: Mana Products, Inc., Long Island City, NY (US)

( * ) Notice: Subject to any disclaimer, the term of this patent is extended or adjusted under 35 U.S.C. 154(b) by 107 days.

This patent is subject to a terminal disclaimer.

(21) Appl. No.: 17/505,005

(22) Filed: Oct. 19, 2021

(65) Prior Publication Data

US 2022/0031577 A1 Feb. 3, 2022

Related U.S. Application Data

(63) Continuation of application No. 16/735,343, filed on Jan. 6, 2020, now Pat. No. 11,147,749, which is a continuation of application No. PCT/US2019/059278, filed on Oct. 31, 2019, and a continuation-in-part of application No. 16/151,735, filed on Oct. 4, 2018, now abandoned.

(60) Provisional application No. 62/753,693, filed on Oct. 31, 2018, provisional application No. 62/567,938, filed on Oct. 4, 2017.

(51) Int. Cl.
| | | |
|---|---|---|
| *A61K 8/02* | (2006.01) | |
| *A61K 8/25* | (2006.01) | |
| *A61K 8/37* | (2006.01) | |
| *A61K 8/73* | (2006.01) | |
| *A61K 8/96* | (2006.01) | |
| *A61Q 5/00* | (2006.01) | |

(52) U.S. Cl.
CPC ............... *A61K 8/022* (2013.01); *A61K 8/25* (2013.01); *A61K 8/37* (2013.01); *A61K 8/732* (2013.01); *A61K 8/965* (2013.01); *A61Q 5/008* (2013.01)

(58) Field of Classification Search
CPC . A61K 8/022; A61K 8/25; A61K 8/37; A61K 8/732; A61K 5/008; A61K 8/965
See application file for complete search history.

(56) References Cited

U.S. PATENT DOCUMENTS

| | | | | |
|---|---|---|---|---|
| 5,641,480 | A * | 6/1997 | Vermeer | A61Q 5/12 424/70.1 |
| 2017/0319448 | A1* | 11/2017 | Aubert | A61Q 5/02 |
| 2018/0153782 | A1* | 6/2018 | Desale | A61Q 5/02 |

FOREIGN PATENT DOCUMENTS

WO WO 2013/175221 * 11/2013

* cited by examiner

*Primary Examiner* — Shirley V Gembeh
(74) *Attorney, Agent, or Firm* — Winthrop & Weinstine, PA; Alicia Griffin Mills; Nadeem W. Schwen

(57) ABSTRACT

A method of providing a treatment for cleaning and removing oils from hair includes providing a cosmetic that includes a blend of a powder phase including at least two absorbents selected from the group of mica, silica, starch, talc, kaolin and zeolite, and at least one emollient with a solvent phase. The blended powder and solvent phases are formed into a dry shampoo product adapted for manual application to the hair. A porous mold may be used to provide the cosmetic. Techniques may be applied to other forms of cosmetic compositions.

17 Claims, 11 Drawing Sheets

DRY COMPOSITION FOR AND METHODS FOR FABRICATION OF DRY COMPOSITIONS

CROSS-REFERENCE TO RELATED APPLICATIONS

The present patent application is a continuation of and claims the benefit of priority to U.S. patent application Ser. No. 16/735,343, filed Jan. 6, 2020, now U.S. Pat. No. 11,147,749, issued Oct. 19, 2021, which in turn is a continuation of and claims the benefit of priority to International Application No. PCT/US2019/059278, filed Oct. 31, 2019, which in turn claims the benefit of priority of U.S. Provisional Patent Application Ser. No. 62/753,693, filed Oct. 31, 2018. The present patent application is a continuation of and claims the benefit of priority to U.S. patent application Ser. No. 16/735,343, filed Jan. 6, 2020, now U.S. Pat. No. 11,147,749, issued Oct. 19, 2021, which in turn is a continuation-in-part of and claims the benefit of priority to U.S. patent application Ser. No. 16/151,735, filed Oct. 4, 2018, which in turn claims the benefit of priority of U.S. Provisional Patent Application Ser. No. 62/567,938, filed Oct. 4, 2017. Each of the foregoing patent applications is incorporated by reference herein in its entirety for any purpose whatsoever.

BACKGROUND

1. Field of the Disclosure

The present disclosure relates to health and cosmetic treatment methods, and in particular, relates to dry shampoo powder compositions as well as methods for fabrication of other dry cosmetic compositions.

2. Description of the Related Art

Most hair cleaning products, such as shampoos, are offered to consumers in liquid or gel form. One of the disadvantages of such products is that use requires wetting of the hair, and a subsequent rinsing from the hair. Although liquid hair products are effective for removing oil and dirt, these products often include surfactants that may damage hair or strip hair of color. Use can be inconvenient and may require other care to restore hair to a desired look.

As an alternative, various dry shampoos have been offered on the market for cleaning hair. Typically, dry shampoo is sold in loose powder or aerosol form. Although use of dry shampoo may be less involved, currently offered forms are difficult to apply efficiently when specific areas of hair are targeted. A form of dry shampoo that is easy to control and apply would be useful to many individuals that are on-the-go.

A variety of other cosmetic products such as blush and foundation products have long been offered to consumers in solid form. Many of these cosmetic products are substantially water or moisture free. Unfortunately, preparation often calls for staged manufacturing processes, such as compression with an expensive press, and subsequent temperature cycling to provide a finished product.

Accordingly, there is a need for an improved manufacturing process that provides solid forms of cosmetics. Preferably, the process results in a variety of products that are compact, convenient to carry, maintain their integrity during use and provides for a high degree of user control when applied as intended.

SUMMARY

The present disclosure provides a method of providing a treatment for cleaning and removing oils from hair which comprises blending a powder phase including at least two absorbents selected from the group of mica, silica, starch, talc, kaolin and zeolite, and at least one emollient with a solvent phase. The blended powder and solvent phases are formed into a dry shampoo tablet adapted for manual and direct application to the hair.

Thus, it will be appreciated that the disclosure also describes a mold for fabricating a solid form cosmetic. The mold can include a geometry suited for molding cosmetic material into a finalized cosmetic product. The mold can include a thermoplastic material with a pore size having a transverse dimension that ranges, for example, between about 7 micrometers and 150 micrometers; between about 10 micrometers and 80 micrometers; and between about 25 micrometers and 40 micrometers. The mold can include one or more of ultra-high molecular weight polyethylene (UHMWPE), high-density polyethylene (HDPE), polypropylene (PP), polytetrafluoroethylene (PTFE), polyvinylidene fluoride (PVDF), ethylene vinyl acetate (EVA), polyethersulfone (PES), and polyurethane (PU) and PE/PP co-polymer.

As will further be appreciated, methods are disclosed for fabricating a solid form cosmetic, as well as the resulting solid form cosmetic.

An illustrative method can include blending a powder phase including at least two absorbents selected from the group of mica, silica, starch, talc, kaolin and zeolite, and at least one emollient, with a solvent phase to provide a slurry, disposing the slurry into a porous mold, and curing the slurry within the mold. The cosmetic can include a dry shampoo, blush, foundation, eye shadow, and the like. The mold can include a thermoplastic material with a pore size diameters ranging, for example, between about 7 micrometers and 150 micrometers, between about 10 micrometers and 80 micrometers and between about 25 micrometers and 40 micrometers, in each case in increments of one micrometer, as desired. The mold can include one or more of ultra-high molecular weight polyethylene (UHMWPE), high-density polyethylene (HDPE), polypropylene (PP), polytetrafluoroethylene (PTFE), polyvinylidene fluoride (PVDF), ethylene vinyl acetate (EVA), polyethersulfone (PES), polyurethane (PU) and PE/PP co-polymer.

In another embodiment, the present disclosure also provides a method of providing a treatment for deodorizing hair which comprises blending a solvent phase with a powder phase including a) at least two absorbents selected from the group of mica, silica, starch, and talc; and kaolin; b) zeolite; and c) at least one emollient. The blended powder and solvent phases are formed into a dry deodorizing tablet adapted for manual application to the hair.

In addition, the present disclosure provides a method of providing a treatment for hair which comprises blending a powder phase including at least two absorbents selected from the group of mica, silica, starch, talc, kaolin and zeolite, at least one emollient, and at least one colorant or highlighting component with a solvent phase. The blended powder and solvent phases are formed into a dry tablet adapted for manual application to the hair.

BRIEF DESCRIPTION OF THE FIGURES

The features and advantages of the disclosure are apparent from the following description taken in conjunction with the accompanying drawings in which.

DETAILED DESCRIPTION

Figure 1:
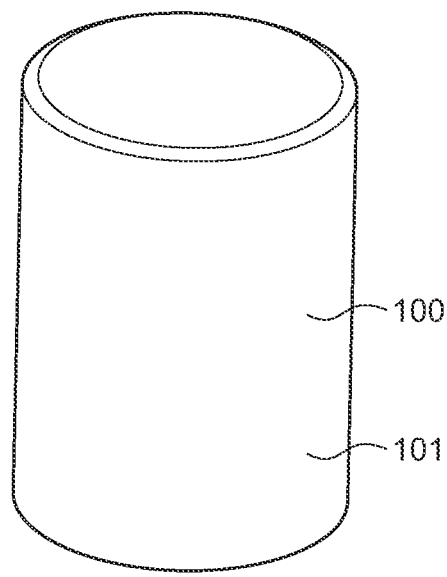
FIG. 1 is a perspective view of a cosmetic in a solid form.

Disclosed herein are compositions of matter, methods of manufacture and products of manufacture that provide users with various forms of cosmetic materials (hereafter "cosmetic" or "cosmetics"). Examples of cosmetics that may be fabricated according to the techniques disclosed herein include dry shampoo, foundation, blush stick and eye shadow.

As an overview, techniques for fabricating the cosmetics include use of a porous mold. A composition for a particular type of cosmetic is disposed into an appropriately shaped porous mold in a slurry form. Generally, the slurry form includes a "powder phase" and a "solvent phase." The ingredients of the powder phase may be varied according to the particular type of cosmetic. Likewise, ingredients of the solvent phase may be varied according to the particular type of cosmetic. Broadly, the solvent phase may include solvents such as water and may include other appropriate solvents to aid in the mixing and shaping of the cosmetic composition.

Once the porous mold has been filled and sealed as deemed appropriate, the slurry is then cured. In one example, a negative pressure is applied to the filled porous mold. The negative pressure, with or without an accompanying thermal cycle, causes the solvent phase to migrate from the composition, leaving a cosmetic that is in a solid form.

The porous mold may be provided in a variety of forms, thus resulting in cosmetics of a solid form that may exhibit a variety of desirable and/or ornamental shapes. In some embodiments, the resulting cosmetic includes surface texturing and/or patterns. Additionally, as the materials chosen for the porous mold may often exhibit a low coefficient of friction, release of the cosmetic materials from the porous mold is reliably achieved and few, if any, defects are realized.

Examples of base compositions (i.e., the powder phase) for the cosmetic materials are provided in Table I. Included are compositions suited for use as dry shampoo, blush stick and eye shadow. Examples of solvent phase compositions for the cosmetic materials are provided in Table II. Included are compositions suited for use as the solvent phase for the dry shampoo, blush stick and eye shadow compositions of Table I.

TABLE I

Cosmetic Compositions for Porous Mold

| Dry Shampoo | Range by weight percent | |
|---|---|---|
| Material | Low | High |
| Mica | 10 | 60 |
| Silica | 5 | 40 |
| Corn starch | 5 | 20 |
| Rice starch | 5 | 20 |
| Talc | 1 | 10 |
| Kaolin (clay) | 1 | 10 |
| Zeolite | 1 | 5 |
| Isodecyl neopentanoate | 1 | 10 |
| Iron oxides | 5 | 30 |
| Preservatives | As needed | As needed |
| Fragrance | As needed | As needed |

| Blush | Range by weight percent | |
|---|---|---|
| Material | Low | High |
| Mica | 10 | 60 |
| Silica | 5 | 20 |
| Corn starch | 5 | 20 |
| Talc | 1 | 10 |
| Lauroyl lysine | 1 | 5 |
| Isodecyl neopentanoate | 1 | 10 |
| Iron oxides | 5 | 15 |
| Preservatives | As needed | As needed |
| Fragrance | As needed | As needed |
| D&C red #7 lake | 5 | 10 |
| D&C red #6 | 5 | 10 |
| D&C red #28 lake | 1 | 5 |

| Eye Shadow | Range by weight percent | |
|---|---|---|
| Material | Low | High |
| Mica | 10 | 60 |
| Silica | 5 | 20 |
| Corn starch | 5 | 20 |
| Talc | 1 | 10 |
| Lauroyl lysine | 1 | 5 |
| Isodecyl neopentanoate | 1 | 10 |
| Iron oxides | 5 | 30 |
| Preservatives | As needed | As needed |
| Fragrance | As needed | As needed |

TABLE II

Solvent Phase Compositions for Porous Mold

| Dry Shampoo | Range by weight percent | |
|---|---|---|
| Material | Low | High |
| Water | 90 | 100 |
| Glycerin | 2 | 10 |
| Carageenan | 0.1 | 1 |
| Xanthan gum | 0.1 | 1 |
| Preservative | As needed | As needed |

| Blush Stick | Range by weight percent | |
|---|---|---|
| Material | Low | High |
| Water | 90 | 100 |
| Glycerin | 2 | 10 |
| Carageenan | 0.1 | 1 |
| Xanthan gum | 0.1 | 1 |
| Preservative | As needed | As needed |

| Eye Shadow Stick | Range by weight percent | |
|---|---|---|
| Material | Low | High |

TABLE II-continued

Solvent Phase Compositions for Porous Mold

| Water | 90 | 100 |
| --- | --- | --- |
| Glycerin | 2 | 10 |
| Carageenan | 0.1 | 1 |
| Xanthan gum | 0.1 | 1 |
| Preservative | As needed | As needed |

Referring now to FIG. 1, aspects of a cosmetic material 100, or simply a "cosmetic 100" are shown. In this example, the cosmetic 100 includes a dry shampoo composition that is provided as a shampoo stick 101. In this illustration, the shampoo stick 101 is separated from a dispenser and has the appearance of an elongated cylinder.

Figure 2:
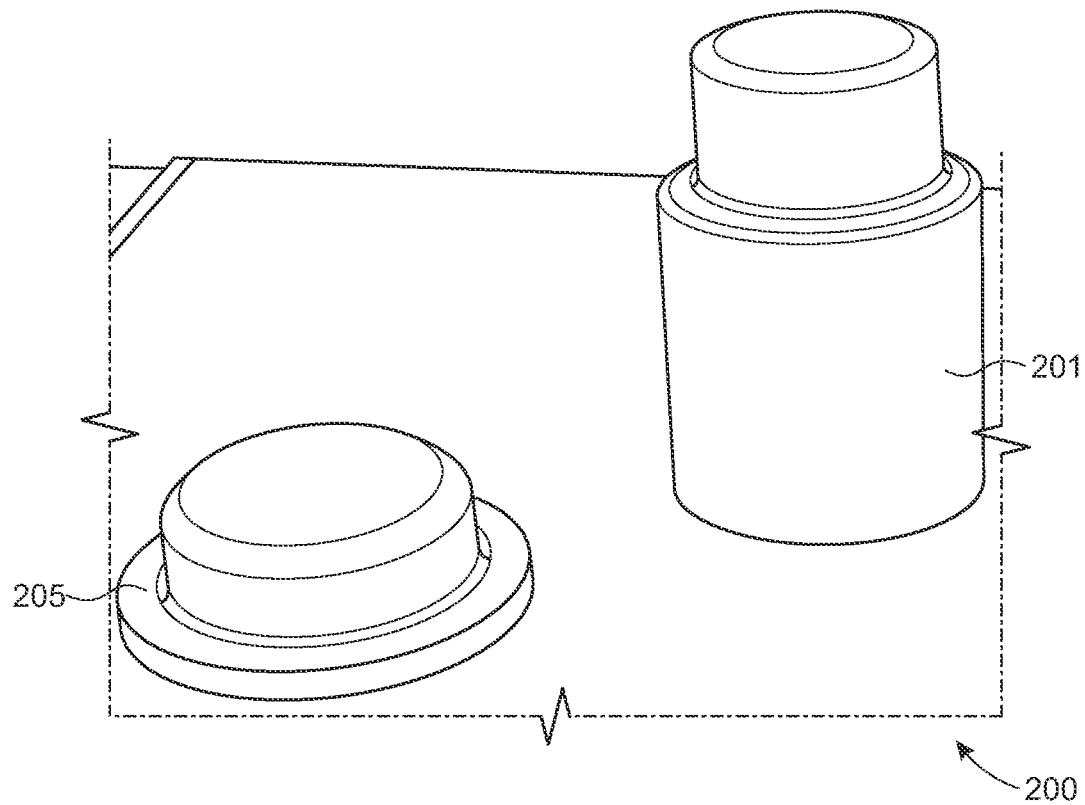
FIG. 2 is a perspective view of a mold for fabricating the cosmetic of FIG. 1.
Figure 3:
FIG. 3 is a photomicrograph showing microstructure of a cross-section of porous polyethylene (PE) for the mold of FIG. 2.

Referring now also to FIG. 2, aspects of an exemplary mold 200 for fabricating the shampoo stick 101 of FIG. 1 are shown. In this example, the mold 200 includes a cylindrically shaped body 201 with open ends (i.e., an annular cylinder). The body 201 and at least one end cap 205 are formed of a porous material. In one embodiment, the porous material is a thermoplastic material, such as a form of polyethylene (PE). In general, porous PE is considered a strong, lightweight thermoplastic with strong chemical resistance. The mold 200 may be made from standard polyethylene grades with pore size diameters ranging from 7 to 150 micrometers. In some embodiments, the pore size ranges between about 10 to 80 micrometers. In some other embodiments, the pore size ranges between about 25 to 40 micrometers. In some embodiments, the pore size values can be increased to 300 micrometers.

Generally, the porous material selected is composed of pores whose cavities are connected to one another, permitting fluidic communication throughout the interior. Porous plastic products may be fabricated from various thermoplastic materials. Generally, the porous plastic products exhibit a broad range of properties. As examples, ultra-high molecular weight polyethylene (UHMWPE), high-density polyethylene (HDPE), polypropylene (PP), polytetrafluoroethylene (PTFE), and polyvinylidene fluoride (PVDF) may be used as the base materials for the mold 200. Other materials include, without limitation, ethylene vinyl acetate (EVA), polyethersulfone (PES), polyurethane (PU) and PE/PP co-polymer.

Figure 4A:
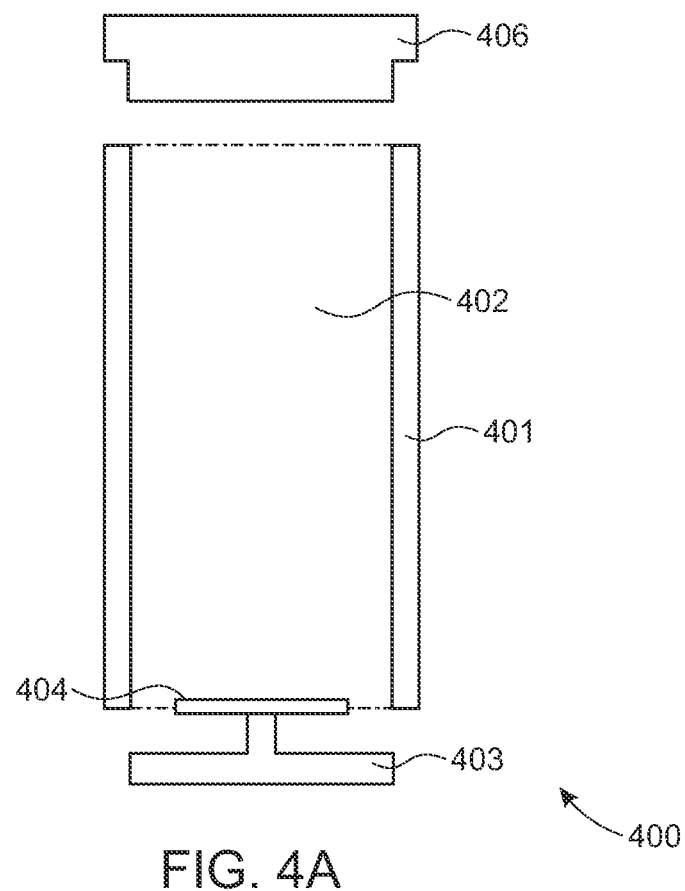
FIGS. 4A, 4B and 4C, collectively referred to herein as FIG. 4, depict aspects of process for molding the cosmetic of FIG. 1.
Figure 4B:
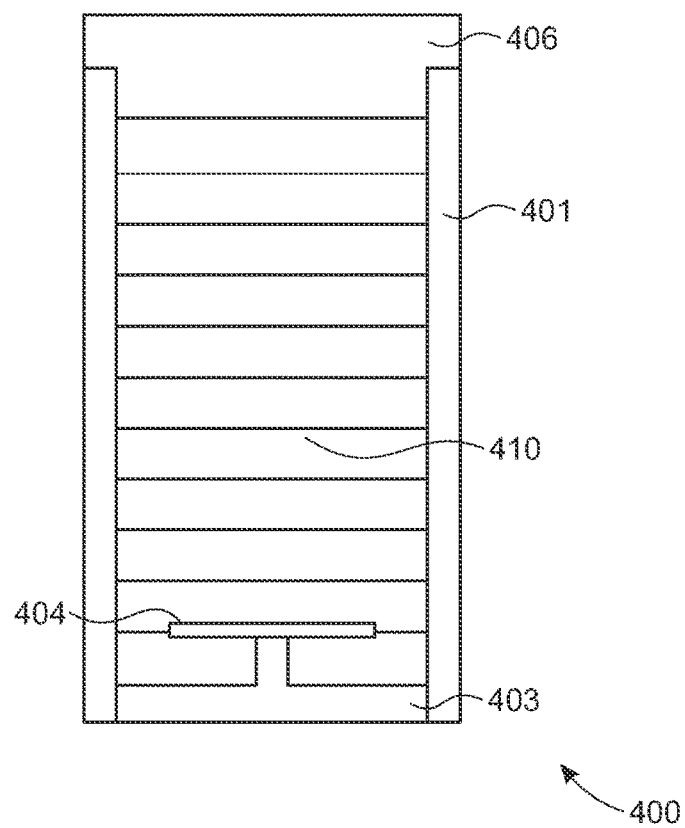
Figure 4C:
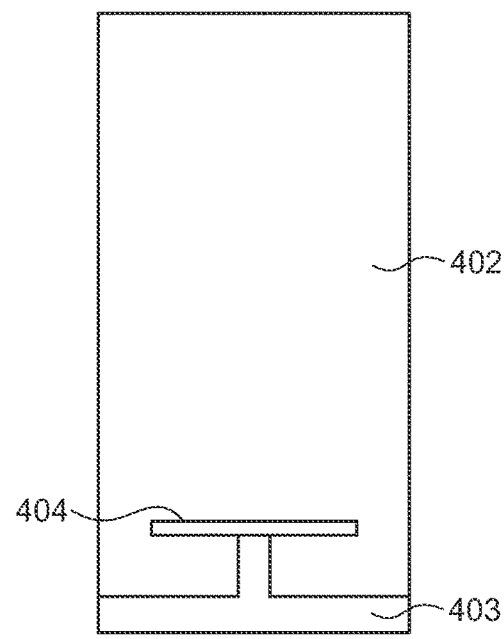

FIGS. 4A, 4B and 4C, collectively referred to as FIG. 4, depict another embodiment of the mold 400. In FIG. 4, the mold 400 and the product derived therefrom are shown in cross-sectional views from the side.

In FIG. 4A, the mold 400 includes the body 401, a removable top or cap 406 and a removable bottom or base 403. The base 403 may include a pedestal onto which an anchor 404 is disposed. The base 403 is inserted into a bottom end of the body 401 and the cap 406 may be disposed into the body 401 (see FIG. 4B) or over the body 401 (see FIG. 2 for this style). A chamber 402 is formed therewithin.

Referring to FIG. 4B, aspects of a technique for forming the shampoo stick 101 are shown. In this example, the base 403 is mated with the body 401. A slurry of product mix is then disposed within the chamber 402 prior to sealing the mold 400. When the cap 406 is applied, a degree of compression may be applied to the product mix. Once the cap 406 has been applied, the chamber 402 is sealed with the cap 406, the mold 400 may be heated if desired. In one embodiment, the mold 400 is then heated to a temperature of about fifty degrees Celsius (50° C.).

The filled mold 400 may be maintained in a negative pressure environment during the heating process. Thus, at least a portion of the solvent phase may be actively withdrawn from the product mix by virtue of the porous material. After the heating cycle has concluded, the cap 406 is removed and the base 406 with shampoo stick 101 disposed thereon may be extruded from the body 401. The shampoo stick 101 may then be disposed within a variety of dispensers for consumer use.

In some embodiments, the mold 400 may include a body 401 that includes various parts. More specifically, the mold 400 may be a multi-part mold, such as a case that may be clamped together for the processing of the cosmetic. Release of a finished cosmetic from the mold 400 will simply call for release of the clamping such that the mold is separable from the cosmetic. In some of these embodiments, manufacturers are capable of offering interesting, convenient or ornamental shapes of cosmetic products. Examples of shapes that may be provided include, without limitation, tablets that may be useful for discrete application of dry shampoo. In some embodiments, the tablets may be provided with dimensional aspects such as by being shaped as a branding icon.

Figure 5:
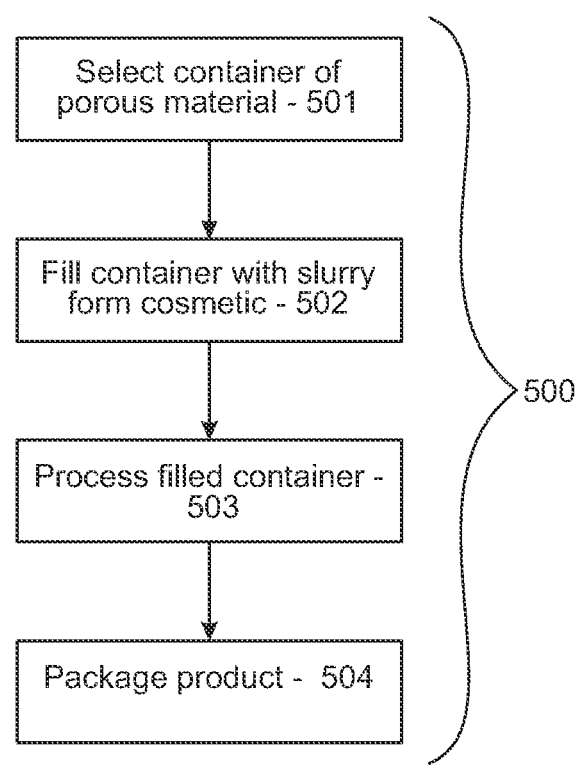
FIG. 5 is a flow chart depicting aspects of an exemplary process for molding the cosmetic of a solid form shown in FIG. 1.

FIG. 5 is a flow chart that sets forth an exemplary process for manufacturing a cosmetic product 500. In a first step 501, a suitably proportioned container formed of porous material with a suitable porosity is selected. In a second step 502, the container is filled with a slurry form of the cosmetic product. In a third step 503, the filled container is processed. Processing may include controlling various environmental factors such as heating and cooling cycles as well as ambient pressure. In a forth step 504, the finalized product is packaged for consumer use.

Generally, the process for manufacturing a cosmetic product 500 results in a cosmetic 100 that may be provided in a form that is convenient to carry and easy to use.

Figure 6:
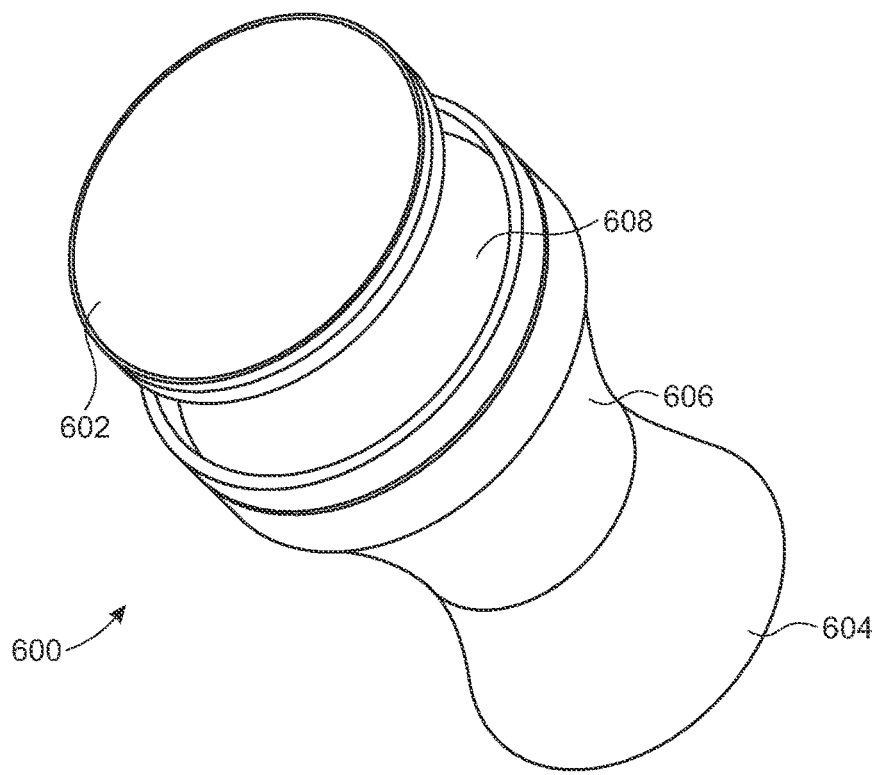
FIG. 6 is a perspective diagram depicting another embodiment of the cosmetic in a dispenser.

FIG. 6 is a perspective view of an embodiment of a dry hair treatment product 600 that includes a product such as the dry shampoo composition. In this example, the hair treatment product 100 includes a disc-shaped tablet (hereinafter referred to as the "shampoo tablet") 602. In some embodiments the shampoo tablet may 602 be approximately 1 to 3 inches in diameter and 0.5 to 1.2 inches in thickness. The shampoo tablet 602 may also be formed in other sizes. In the depicted embodiment, an ergonomically-designed container 604, which may be generally cylindrical, but may also include a narrowed middle or waist region 606 for manual handling, has at its top a disc-shaped platform space 608 in which the shampoo tablet 602 may be stored. The container 604 may also function as an applicator as the shampoo tablet 602 may be made to fit tightly within the platform 608 so that it does not fall out of the platform when the container is turned when applying the shampoo tablet to specific areas of hair. It is noted that the container shown in FIG. 6 is exemplary and that other containers having different shapes and functionality may be used. For example, in some embodiments, the platform 608 may be height-adjustable using mechanisms well known in the art.

Figure 7:
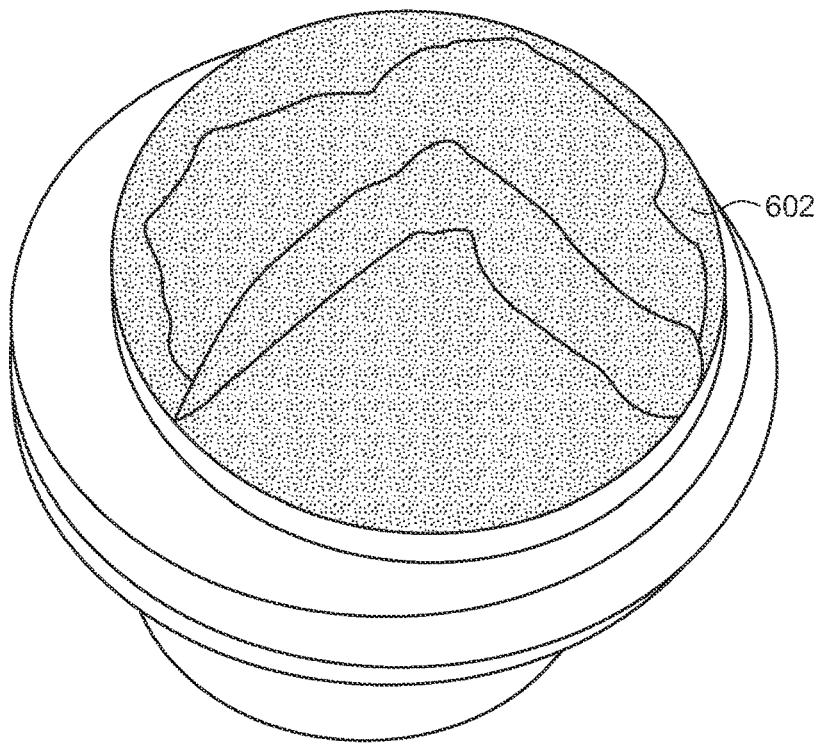
FIG. 7 is a photograph of the embodiment of the cosmetic depicted in FIG. 6, where the cosmetic has been segmented.
Figure 8:
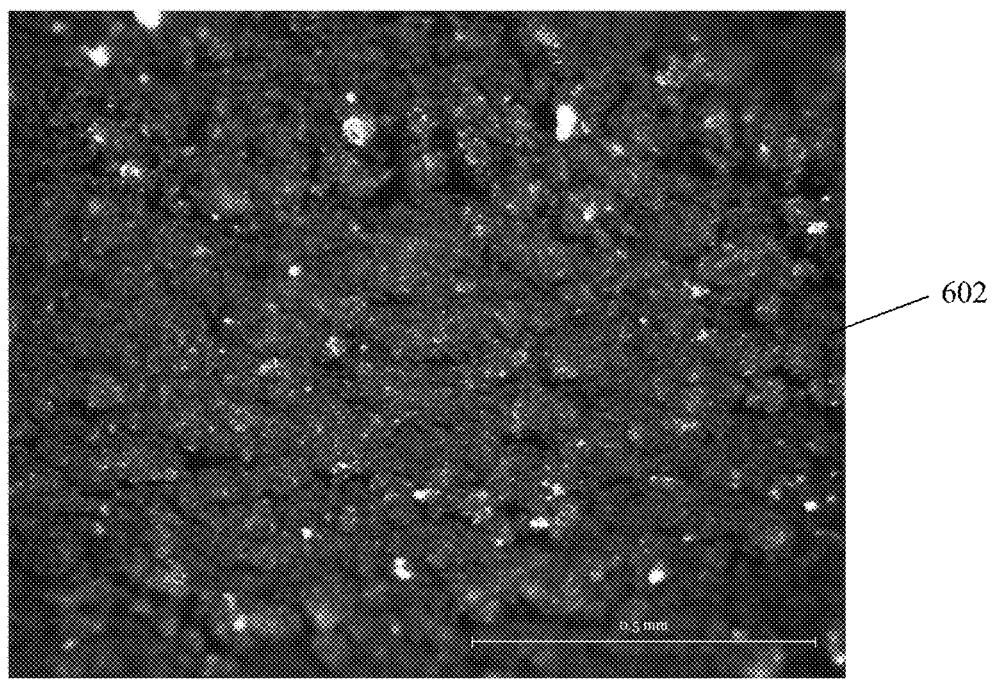
FIGS. 8 through 15 are photomicrographs showing microstructure of a cross-section of the composition of matter contained in the cosmetic of FIGS. 6 and 7.
Figure 9:
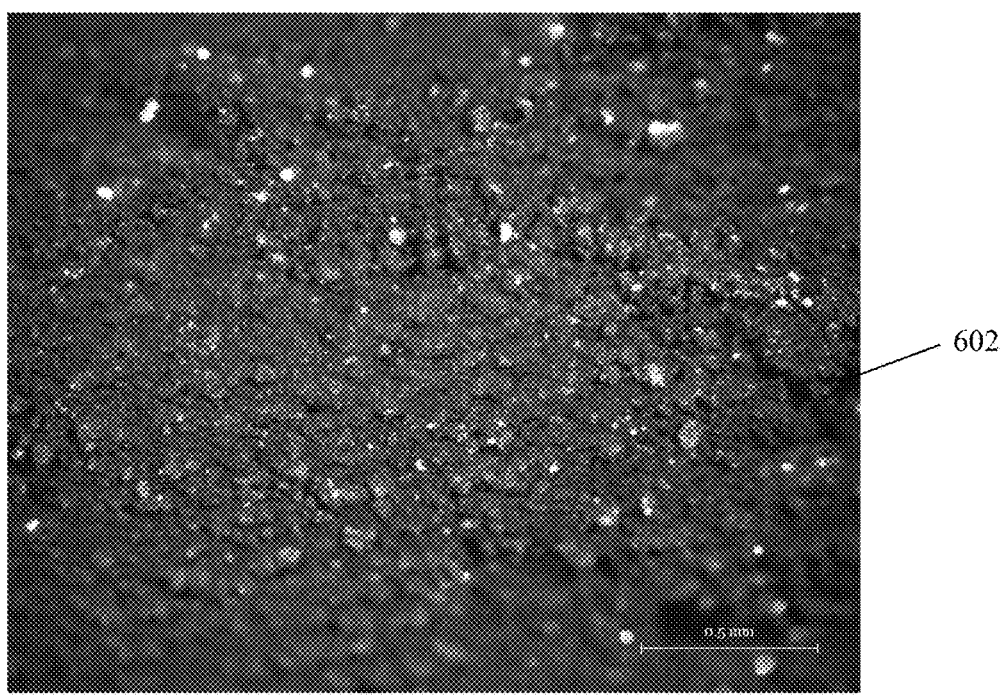
Figure 10:
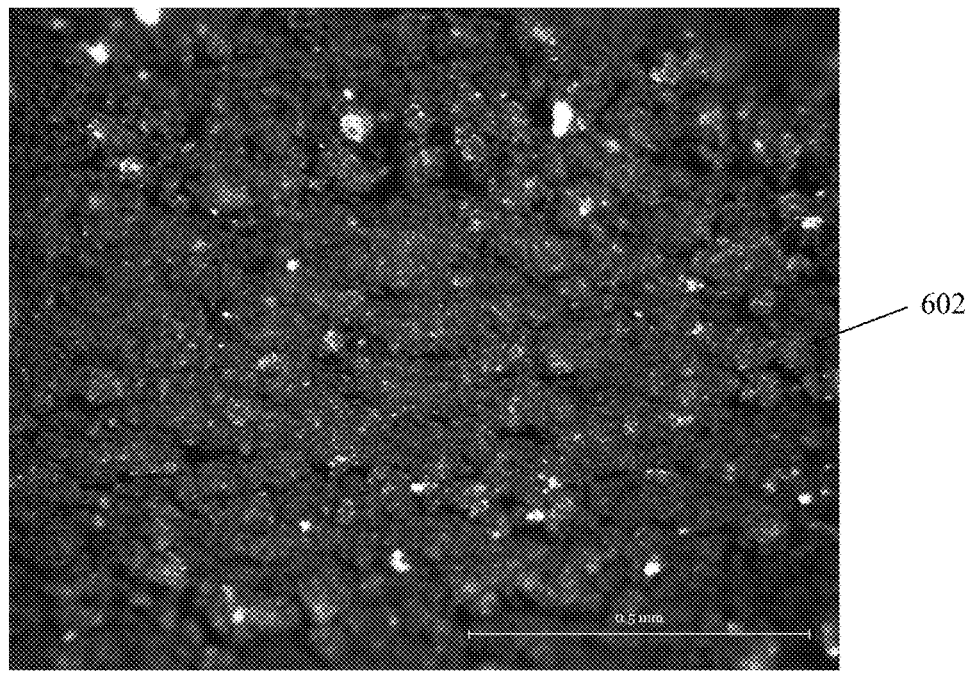
Figure 11:
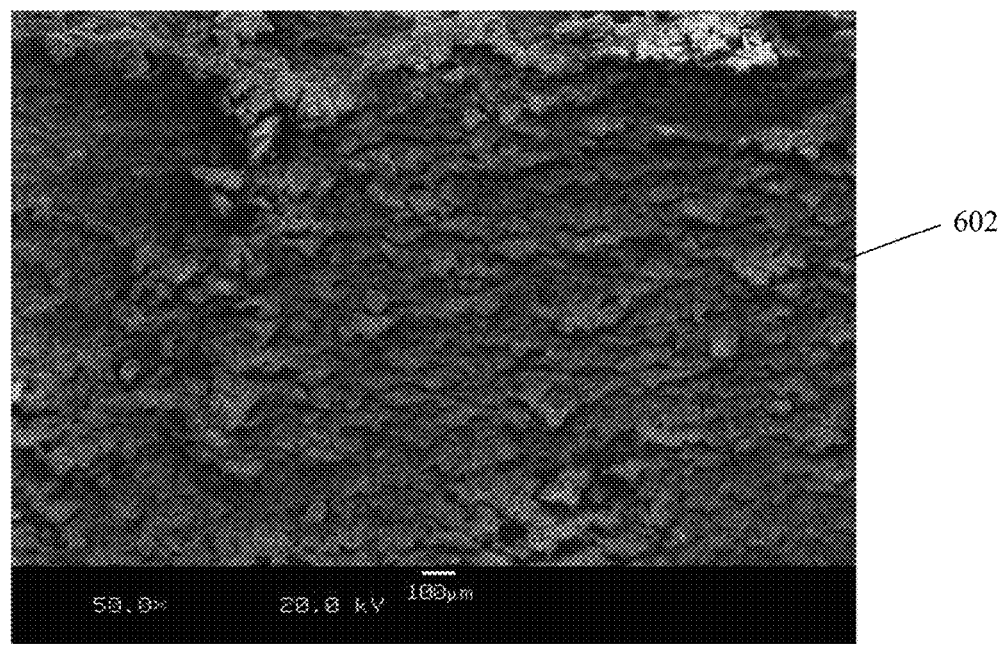
Figure 12:
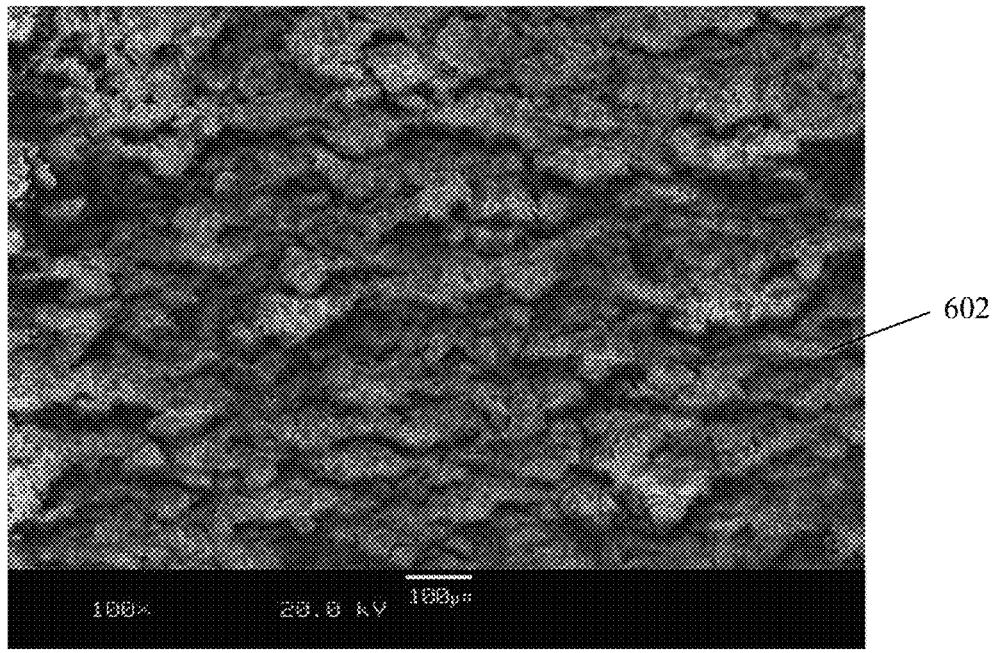
Figure 13:
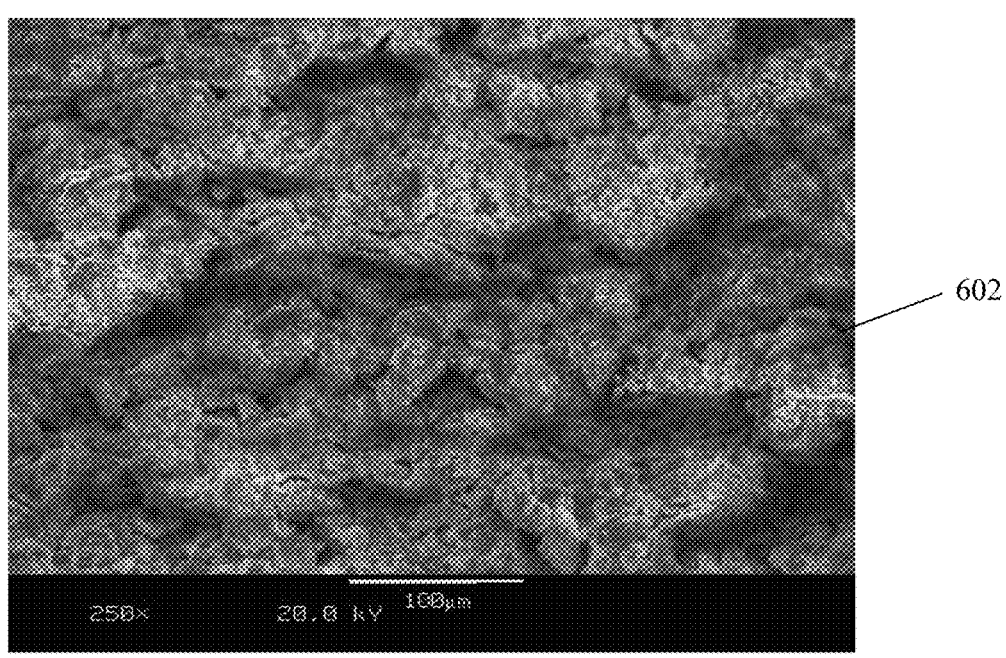
Figure 14:
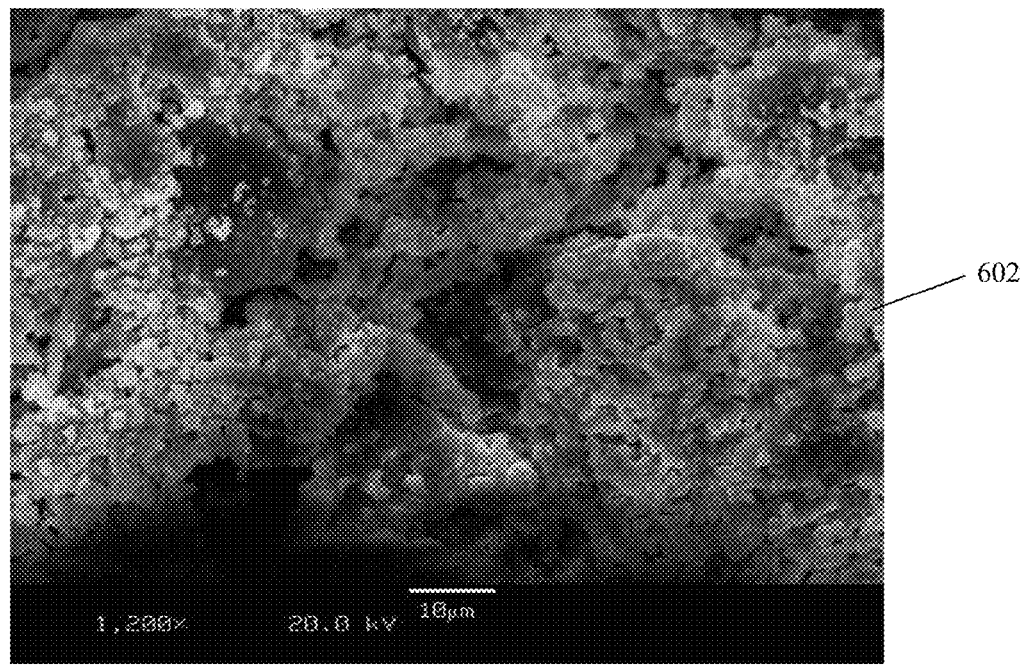
Figure 15:
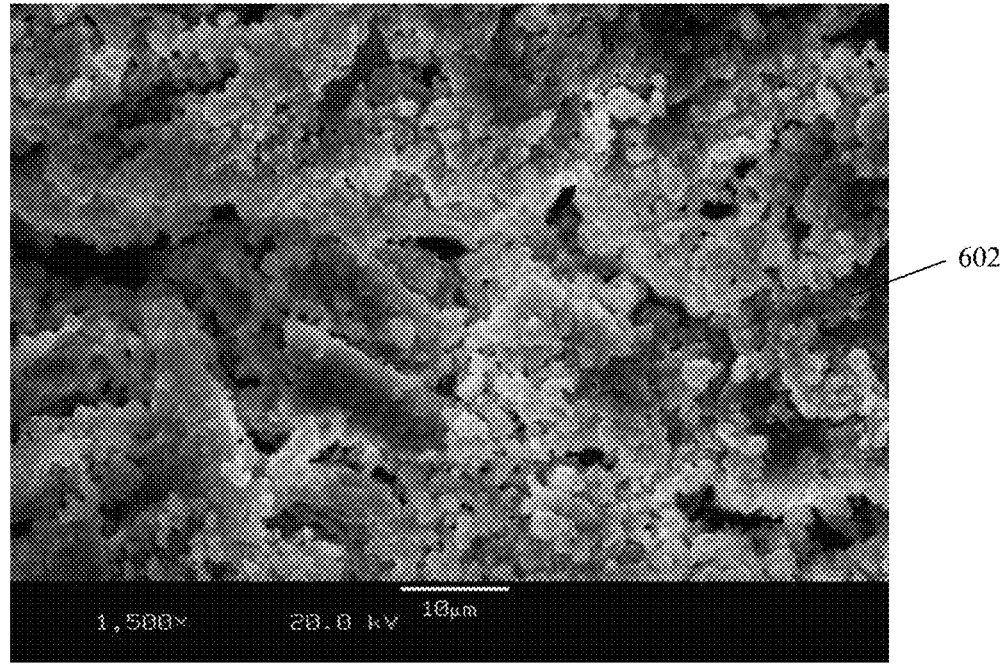

An example of the shampoo tablet 602 is shown in FIG. 7. In this example, the shampoo tablet 602 has been partially segmented for testing. The fine-grained texture of the shampoo tablet is shown in FIG. 8 which is a photomicrograph of a cross-section of the shampoo tablet 602. As can be discerned, the texture is shiny and smooth overall, while the numerous visible crevices and grains indicate the granularity of the shampoo material which provides enhanced absorbance. FIGS. 9 through 15 are additional photomicrographs at various magnifications.

The surface of each cross section of a cosmetic sample fabricated in accordance with the teachings herein were imaged. Imaging was performed at various magnifications (50×, 100×, and 250×).

Images were obtained with both optical systems and a scanning electron microscope (SEM). Optical images show the color of the sample, however the microscope used for imaging lost focus at about 100×. The images taken with the scanning electron microscope (SEM) show particles and the requested magnifications. The SEM images are in black and white.

Generally, and for some embodiments, the mica component of the powder phase, which may be the largest by weight percentage in a given composition imparts a dry texture to the shampoo tablet, and also imparts a natural shine to hair. The silica also provides texture and useful oil-absorbent properties, imparting smoothness. The modified starch, which is preferably a tapioca starch, but may also comprise corn and/or rice starch improves aesthetic effects by absorbing oily and greasy hair components. Talc and clay have oil and grease mitigation properties similar to the modified starch and can be used in addition to, or as a substitute for the starch. Zeolite is effective at capturing small particles and is particularly useful at reducing odors, e.g., odors arising from cosmetic products. Zeolite absorbs a variety of water-based and anhydrous compositions. Isodecyl neopentanoate acts as a binding ester and may be used to improve emolliency and the even distribution of the finished product, and may also improve aesthetic effects. In some embodiments, a silicon containing material such as dimethicone may be used as an emollient. Lauroyl lysine is an amino-acid based powder that acts as an anti-static agent and aids in the distribution of the other components.

In another embodiment that does not involve use of the porous mold (200, 400), the shampoo tablet 602 may be produced by the following exemplary process. First, the powder phase and the solvent phase are mixed well in a container, such as a kettle. The powder phase is mixed with the solvent phase according to a specific ratio from approximate 1:2 to 2:1 depending on desired properties. Once the phases are mixed into a homogeneous and uniform bulk phases (i.e., the "slurry"), the bulk phase is pumped and transferred to a feed nozzle and injected onto a ceramic or plastic substrate. The bulk phase material is then pressed into shaped tablets using a punch, while simultaneously a negative vacuum is created to extract most of the solvent. The pressed material is then then transferred onto trays which are then feed into a heater and heated at approximately 25 degrees Celsius to about 75 degrees Celsius (° C.), depending upon the solvent used, until the shampoo tablets 602 are adequately dry.

The resultant shampoo tablet 602 product has the texture of an emollient powder "cake." The feel of the cake balances and combines the granularity of a powder with emollience and smoothness. The granularity increases the surface area of the cake product, providing improved absorbance, while the emollient properties improve aesthetic effects, such as shine and smoothness. As noted above, the shampoo tablet may be applied to specific areas of hair to clean and remove oils from hair fibers, and as a deodorant. Additionally, during production, colorant components may be added to the powder phase, and the resulting shampoo tablets may be used to color or add highlights to specific areas of hair where the tablet is applied.

Importantly, there is no need to rinse the hair after application of the dry shampoo disclosed herein as minimal residue is leftover, and as the hair remains dry.

Having thus introduced aspects of dry shampoo and a process for manufacture thereof, some additional embodiments and/or features are now provided.

In some embodiments, the mold, or portions of the mold, may also serve as a case for the finished cosmetic product. For example, once the manufacturing process has completed, branding may be applied to the body of the mold, such as in the form of a wrapper disposed thereover (not shown). In addition to carrying branding information, the wrapper may provide a moisture barrier to limit moisture intrusion into the cosmetic product.

Cosmetic products fabricated according to the techniques disclosed herein may be provided in a variety of forms (e.g., in varying lengths and/or widths).

Further, while referred to as being a "shampoo stick" in some embodiments, it should be recognized that the cosmetic composition and process for manufacture thereof may be useful for other purposes. For example, a similar process may be used to provide an "eye shadow stick", a "bronzer stick", or the like. More specifically, colors in the form of pigments and/or dyes may be added to the composition which is in turn loaded into a similar mold (albeit of differing proportions). Similarly, the stick cosmetic may be specially formulated and configured for use as foundation or blush.

The final form of the cosmetic need not be limited to stick form. That is, the solid form cosmetic may be provided in any geometry deemed appropriate.

Example 2

The following composition is representative of a further composition that can be used in a stick dispensing format.

| MINERAL CLAY MASK/CLEANSING STICK Ref. No.: EXP-1008173\004 | |
| --- | --- |
| Ingredients | % w/w |
| Mica | 44.54 |
| Silica | 15.00 |
| Aluminum Starch Octylsuccinate | 15.00 |
| Lauroyl Lysine | 1.00 |
| Zinc Stearate | 4.00 |
| Clay | 6.00 |
| Isodecyl Neopentanoate | 9.56 |
| Diisostearyl Malate | 2.70 |
| Iron Oxide (CI 77492) | 0.30 |
| Iron Oxide (CI 77491) | 0.60 |
| Iron Oxide (CI 77499) | 0.10 |
| Phenoxyethanol | 0.70 |
| Caprylyl Glycol | 0.30 |
| Vitamin E Acetate | 0.20 |
| | 100.00 |

It will be appreciated that the percentages of the various constituents can be varied. For example, in some implementations the mica can vary from about 35 to about 55 percent by weight, or any increment therebetween of about one percent. The silica can vary from about 10 to about 20 percent by weight, or any increment therebetween of about one percent. The aluminum starch material can vary from about 10 to about 20 percent by weight, or any increment therebetween of about one percent. The remaining materials can vary from about 10 to about 20 percent by weight, or any increment therebetween of about one percent. One or more of the next five materials, if provided can vary from about one percent to about ten percent, or any increment therebetween of about 0.1 percent. One or more of the remaining materials, if provided, can vary between about 0.01 and 1 percent, or any increment therebetween of 0.01 percent.

Figure 16A:
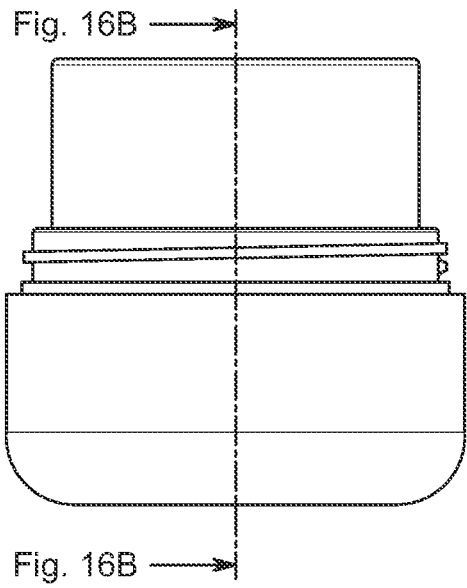
FIGS. 16A-16D and 17A-17D present additional embodiments in accordance with the disclosure.
Figure 16B:
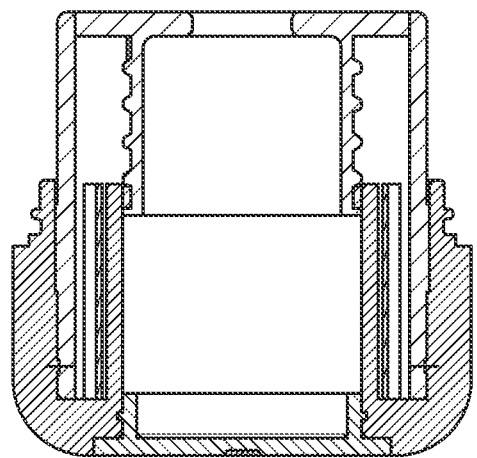
Figure 16C:
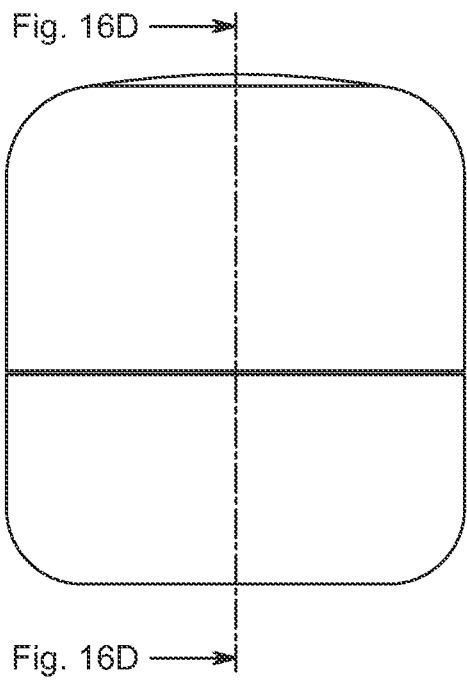
Figure 16D:
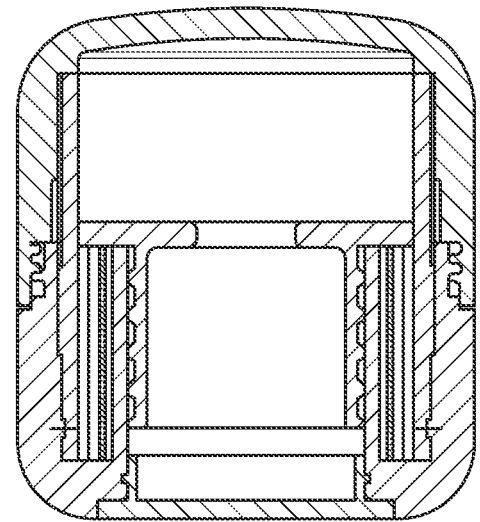

FIGS. 16A-16D and 17A-17D present further embodiments in accordance with the present disclosure. FIG. 16A shows a side view of a further embodiment of a cosmetic stick dispenser in accordance with the disclosure with a covering cap removed, and FIG. 16C displays the embodiment with the cap attached. FIG. 16B shows a cross section along the line of A-A in FIG. 16A, and FIG. 16D shows a cross section along the line B-B in FIG. 16C. As is evident, the dispenser includes a table, or platform, with a downwardly depending cylindrical skirt having a screw thread formed on an outer surface thereof. That threading mates with a complementary inwardly facing thread on an upper end of an upwardly extending cylindrical apron attached to a bottom of the outer housing. The table or platform defines an opening through a center thereof to permit material to be molded through the hole and on top of the platform to hold the material in place by gripping about an inwardly facing periphery of the hole and/or a downwardly facing surface opposite the platform surface that supports the cosmetic stick. An intermediate cylindrical sleeve is received in a rotational snap fit connection between the apron and an outer cylindrical wall so that the sleeve can rotate with respect to the base portion of the housing that includes the inner upwardly extending cylindrical apron and a complementary outer cylindrical wall of the base. The platform includes a boss (not shown) that interfits into a vertical groove in the inner surface of the intermediate sleeve. In use, a user can grip the portion of the intermediate sleeve that extends outwardly and upwardly from the base, and rotate it with respect to the base portion. This causes relative upward axial motion of the platform because the inwardly radially extending thread at the top of the apron rotates with respect to the threading on the platform. The platform is rotationally constrained with respect to the sleeve by virtue of the boss extending into the vertical groove of the sleeve. This causes the relative rotational motion of the base portion with respect to the sleeve and the platform to be transformed into upward or downward relative motion of the platform, depending on the relative directions of rotation of the sleeve and the base.

Figure 17A:
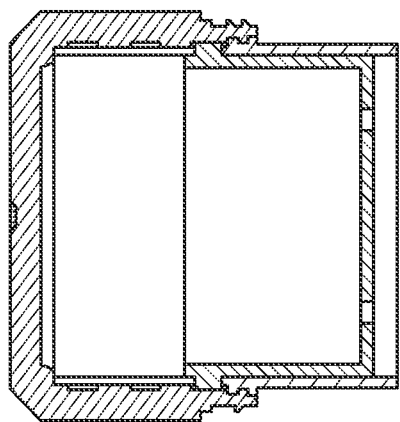
Figure 17B:
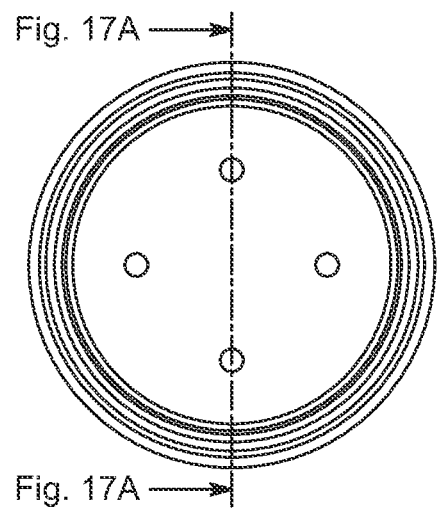
Figure 17C:
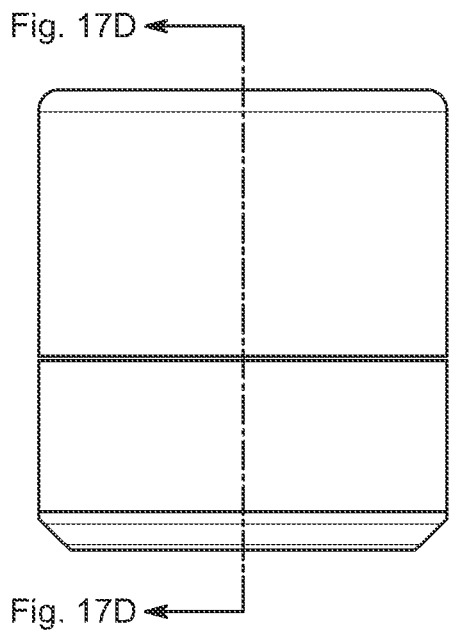
Figure 17D:
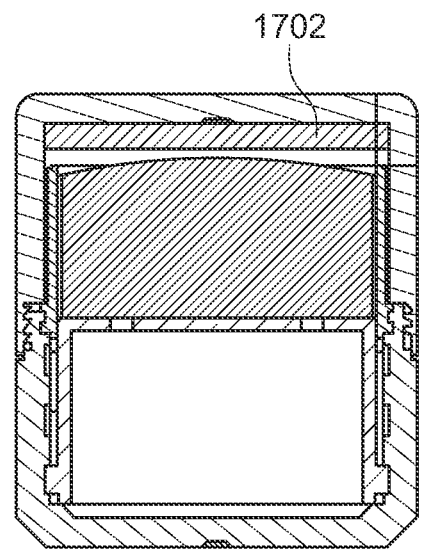

FIGS. 17A-D show an alternative embodiment of a dispenser wherein the platform includes a downwardly depending cylindrical skirt that terminates in one or more radially outwardly extending bosses that are received by a radially inwardly facing thread defined on a radially inwardly facing surface of a cup shaped base portion. The bosses are carried upwards along the threads when relative rotational motion occurs between the platform and the base portion. In the disclosed embodiment, two radially outwardly extending bosses are illustrated in FIG. 17 D at a bottom of the base. Each boss extends through a vertical groove defined on opposing sides of intermediate sleeve portion. Thus, relative rotational motion of intermediate sleeve with respect to the base portion forces the bosses upwardly along the screw thread while they are rotationally constrained by the intermediate sleeve until the platform reaches an uppermost extent as illustrated in FIG. 17A. FIG. 17D illustrates the cosmetic stick in place on top of the platform and contacting the inwardly facing surface of the intermediate sleeve. The platform can be raised by rotating the base with respect to the intermediate sleeve to raise the platform to cause the cosmetic stick to extend beyond the upper end of the intermediate sleeve until the entire cosmetic stick is consumed. In addition, FIG. 17D illustrates a compliant or soft pad or sponge disposed inside the top of the removable cap. Such a spongy material (e.g., polymeric foam) can gently press against the cosmetic stick to protect it from shock and vibration during transport. The embodiment of FIG. 16 can also be provided with such a pad at an upper inner surface of the removable cap. The platform of FIG. 17 can also be provided with holes for molded material to pass into in order to hold the cosmetic stick on the platform.

A variety of modifications of the teachings herein may be realized. Generally, modifications may be designed according to the needs of a user, designer, manufacturer or other similarly interested party. The modifications may be intended to meet a particular standard of performance considered important by that party.

Various other components may be included and called upon for providing for aspects of the teachings herein. For example, additional materials, combinations of materials and/or omission of materials may be used to provide for added embodiments that are within the scope of the teachings herein.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. As used herein, the term "exemplary" is not intended to imply a superlative example. Rather, "exemplary" refers to an embodiment that is one of many possible embodiments.

Where a range of weight percentages of ingredients is described herein, the present disclosure contemplates that any value in increments of 0.1 weight percent between (and including) the endpoints of any such range can be practiced, wherein the total weight of the components of the overall composition total 100 weight percent.

While the disclosure has been described with reference to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method of providing a treatment for cleaning and removing oils from hair without rinsing the hair, comprising:
    providing a powder phase including at least one emollient and at least two absorbents selected from the group of mica, silica, starch, talc, kaolin and zeolite;
    providing a solvent phase;
    blending the powder phase and the solvent phase to form a slurry; and
    forming the slurry into a dry shampoo tablet; and
    removing solvent from the dry shampoo tablet;
    wherein the dry shampoo tablet is adapted for manual application to the hair by pressing the dry shampoo tablet to the hair without wetting the dry shampoo tablet or the hair.

2. The method of claim 1, wherein the step of forming the dry shampoo tablet includes molding and heating the slurry, wherein molding is done using a mold made of a porous material.

3. The method of claim 1, wherein the dry shampoo tablet is formed in the shape of a disc having a diameter of between approximately 1 and 3 inches.

4. The method of claim 1, wherein the emollient includes at least one of isodecyl neopentanoate and a silicon containing material such as dimethicone.

5. The method of claim 1, wherein the powder phase includes zeolite at 1 to 5 weight percentage.

6. The method of claim 1, wherein the powder phase further includes a fragrance component.

7. The method of claim 1, wherein the powder phase further includes a colorant component.

8. The method of claim 1, wherein the powder phases comprises a majority mica.

9. A method of providing a treatment for deodorizing hair, comprising:
blending a solvent phase with a powder phase, wherein the powder phase includes:
at least two absorbents selected from the group of mica, silica, starch, talc, kaolin, and zeolite; and
at least one emollient; and
forming the blended powder and solvent phases into a dry deodorizing tablet; and
removing solvent from the dry deodorizing tablet;
wherein the dry deodorizing tablet is adapted for manual application to the hair la pressing the dry deodorizing tablet to the hair without wetting the dry deodorizing tablet or the hair.

10. The method of claim 9, wherein the step of forming the dry shampoo tablet includes molding and heating the blended powder and solvent phases.

11. The method of claim 9, wherein the dry deodorizing tablet is formed in the shape of a disc having a diameter of between approximately 1 and 3 inches.

12. The method of claim 9, wherein the emollient includes isodecyl neopentanoate.

13. The method of claim 9, wherein the zeolite form 1 to 5 weight percent of the powder phase.

14. A method of providing a treatment for hair, comprising:
providing a powder phase including at least two absorbents selected from the group of mica, silica, starch, talc, kaolin and zeolite, at least one emollient, and at least one colorant or highlighting component;
providing a solvent phase;
blending the powder phase and the solvent phase;
forming the blended powder and solvent phases into a dry tablet; and
removing solvent from the dry tablet;
wherein the dry tablet is adapted for manual application to the hair by pressing the dry tablet to the hair without wetting the hair.

15. The method of claim 14, wherein the step of forming the dry shampoo tablet includes molding and heating the blended powder and solvent phases.

16. The method of claim 14, wherein the dry tablet is formed in the shape of a disc having a diameter of between approximately 1 and 3 inches.

17. The method of claim 14, wherein the emollient includes isodecyl neopentanoate.

* * * * *